United States Patent [19]

Appleford et al.

[11] 4,116,048

[45] Sep. 26, 1978

[54] HARDNESS TESTER

[75] Inventors: David Dale Appleford; Paul Stephen Warwick, both of Swindon, England

[73] Assignee: Monsanto Company, St. Louis, Mo.

[21] Appl. No.: 778,102

[22] Filed: Mar. 16, 1977

[30] Foreign Application Priority Data

Mar. 16, 1976 [GB] United Kingdom ............... 10460/76

[51] Int. Cl.² .............................................. G01N 3/44
[52] U.S. Cl. .................................................... 73/83
[58] Field of Search ................................ 73/81, 83, 94

[56] References Cited

U.S. PATENT DOCUMENTS

| | | | |
|---|---|---|---|
| 2,282,904 | 5/1942 | Tea | 73/81 |
| 2,892,344 | 6/1959 | Sklar | 73/83 |
| 2,938,377 | 5/1960 | Sklar | 73/83 |
| 3,657,921 | 4/1972 | Lang | 73/83 |
| 3,855,848 | 12/1974 | Sidler | 73/81 |
| 4,019,376 | 4/1977 | Iwasaki | 73/81 |

*Primary Examiner*—Anthony V. Ciarlante

[57] ABSTRACT

Hardness tester adaptable to automatic testing of rubber comprising sample support surface, indentor perpendicular to the surface slidably movable within a housing, means for introducing gas under pressure between the indentor and the housing to laterally support the indentor while the sample is subjected to the weight of the indentor only, foot providing a flat datum surface normal to the indentor and with space through which the indentor is movable, means for lowering the foot and indentor in contact with the sample, means to increase the weight on the indentor and means to indicate its downward movement.

2 Claims, 5 Drawing Figures

HARDNESS TESTER

This invention relates to apparatus for measuring the hardness of a material by determining the resistance of the material to indentation. More particularly, the invention relates to apparatus which can be used for determining the hardness of rubber in accordance with various standard methods; for example BS 903 Part A26, ISO R48, ASTM D 1415-74 and DIN 53519.

The essential parts and mode of action of an apparatus in conformity with British Standard BS 903 Part A26 are as follows:

1. An indentor comprising a vertical plunger terminating at its lower end in a rigid ball, and capable of substantially frictionless vertical movement;
2. A rigid foot in the form of an annulus concentric with the indentor and having a lower surface (the datum surface) that is flat and normal to the indentor axis, the foot and any attachments thereto being such as to allow free passage of the indentor, to be capable of substantially frictionless vertical movement, and to be capable of pressing on a test piece with specified force;
3. Means for supporting the indentor so that, except when an indentation measurement is being made, the lowest extremity of the indentor is at least 0.1 mm above the datum surface of the foot;
4. Means for bringing the indentor into contact with the test piece with a specified contact force and means for increasing this force by the amount specified as the indenting force increment;
5. Means for measuring the vertical movement of the indentor relative to the foot.

Factory control tests on hardness used by individual rubber manufactures may depart in some respects from the standard methods, and provided constant test conditions are maintained, useful information on batch to batch variation or departure from a norm may be obtained. There is, however, little room for such departure if test conditions are to be maintained constant and reliable results obtained, and in the type of apparatus where hardness is measured by a weighted probe resting on a sample of the material under test, an arrangement comprising a plunger capable of substantially frictionless vertical movement in a housing, is almost unavoidable. In hardness testers hitherto the usual expedient for minimising the effect of residual friction has been to impose a gentle vibration on the apparatus. Such vibration is undesirable when sensitive means for measuring the displacement of the indentor are employed, however, and the need to include a vibrator is a complication in the design of an automatic apparatus.

In the hardness tester of the present invention, need to provide vibration is avoided.

The present invention provides apparatus for measuring the hardness of a sample of rubber, comprising a sample support surface, an indentor comprising a plunger terminating in a standard probe and having its axis perpendicular to the support surface, a housing within which the plunger is a sliding fit, means for introducing gas under pressure between the bearing surfaces of the plunger and the housing, a foot providing a datum surface that is flat and normal to the indentor axis, the foot being such as to allow free passage of the probe therethrough, means for lowering the foot into contact with a sample, means for lowering the probe into contact with the sample such that the indentor is free standing on the sample and exerts on the sample a determined contact force for a first determined period of time, means applicable to the indentor to increase the weight on the sample by the indenting force increment for a second determine period of time, and means to indicate the downward movement of the indentor during the said second determined period of time.

In a preferred form of the apparatus, the weight which provides the indenting force increment is arranged as a vertically slidable collar around the outer surface of the housing and means are provided to introduce gas under pressure between the bearing surfaces of the housing and of the collar. During the second determined period of time, the collar rests on lateral projections from the indentor which pass through slots in the housing.

The Standard test methods referred to above do not provide for control of the rate at which the foot and the probe are lowered into contact with the sample, nor for control of the manner in which the indenting force increment is applied. We have found that variations in such rates and lack of such control can introduce spurious irregularities into the hardness readings obtained on the same or different rubber samples. Preferred embodiments of the apparatus of the invention accordingly include means for lowering the foot and means for lowering the indentor at controlled rates into contact with the sample, and in the preferred form of apparatus referred to above where the indenting force increment is provided by a vertically slidable collar, means for lowering the collar on to the projections from the indentor at a controlled rate.

The extent of indentation during the period when the sample is subject to the indenting force is conveniently measured using a transducer which provides electrical signals indicative of the position of the indentor relative to the housing, and electrical circuit means including display means, responsive to the said signals and adapted to provide an output signal indicative of the hardness of the sample under test and to present the output signal as a permanent or temporary record. In accordance with a preferred feature of the present invention, the electrical circuit means include a linear analogue to digital convertor which obtains and stores a digital number (contact number) corresponding to the position of the indentor in contact with the sample at the end of the first said period of time, and a non-linear analogue to digital convertor which includes a digital store in the form of a "table" giving the non-linear correlation defined in the Standards between indentation (converted to an analogue input signal) and International Rubber Hardness Degrees presented as a digital output. The contact number is used as a reference level by adding to the contact number progressively larger numbers selected from the store until the sum of the contact number and a given number from the store corresponds to the analogue input at the end of the second said period of time. The sequence of operations during which hardness measurements are carried out at at least three different points on the surface of a sample, namely lowering in succession the foot and the indentor into contact with the sample, adding the indenting force to the weight of the indentor, removing the indenting force after a specified time interval and raising the foot and indentor, rotating the sample support surface to the next testing station, can readily be automated. It is also desirable to include in the automatic system mechanical means for conveying the sample from a convenient feed point on to the support surface, and means for removing the sample from the support surface when the measurements on that sample are completed. A further optional feature is the provision of a store of samples and, as a further part of the automatic system, means to select the samples one at a time from the store and to convey a selected sample to the feed point.

The invention is illustrated by the apparatus shown in the accompanying drawings, in which FIG. 1 is a partially sectionalised elevation;

Figure 2:
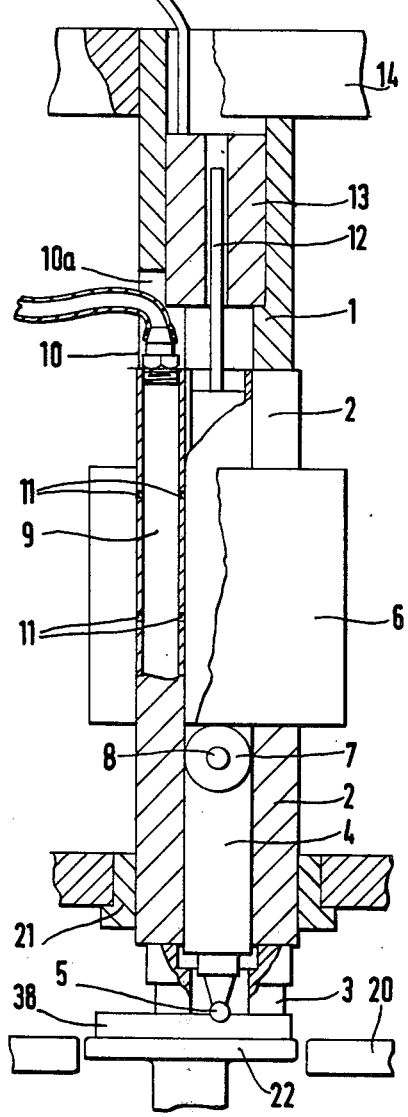
FIG. 2 is a partially sectionalised view of part of the apparatus, from the opposite side to FIG. 1 and with some parts in different positions from those shown in FIG. 1.

The apparatus includes a cylindrical housing having an upper part 1 and a lower part 2. An annular foot 3 is attached to the lower end of part 2, and an indentor comprising a plunger 4 terminating at its lower end in a ball 5 of standard dimensions is a sliding fit within the lower part 2 of the housing. The incremental load is provided by a cylindrical collar 6 of standard weight which is a sliding fit over the outside of the housing part 2. An upwardly extending arm terminating in a hook 6a is attached to the upper end of the collar 6. During the second determined period of time in the test and in the position shown in FIG. 2 the collar rests on rollers 7 mounted at the ends of a shaft 8 which is fixed diametrically through the plunger 4. The shaft 8 is accommodated in a slot cut diametrically through the housing and of a size to permit relative vertical movement of the housing and the plunger.

The housing has three vertical manifolds, one of which is shown at 9, closed at their lower ends and having at their open upper ends connectors 10 for connection to a compressed gas supply. Each connector 10 is located in a slot 10a in the wall of the housing. From the manifold 9 transverse passages 11 extend to both the inner and outer surfaces of the housing.

Measurement of the position of the indentor relative to the foot is measured by a linear variable displacement transducer, the core 12 of which forms a coaxial vertical extension of the plunger 4, and the body 13 of which is a fixed coaxial insert in the upper part 1 of the housing.

The upper part 1 of the housing is attached at its upper end to a moveable crosshead 14 having a linear bearing 15 at each end to allow the crosshead to slide on two vertical standards 16 which are bolted at their upper ends to a fixed crosshead 17. At their lower ends, the standards are secured to a table 18 having legs 19 fixed to a base plate 20. The table 18 has a circular opening lined by an annular bush 21 which acts as a bearing for the lower end of the housing 2. A further circular opening is provided in the base plate 20 to accommodate a turntable 22 set eccentrically relative to the axis of the housing.

Figure 1:
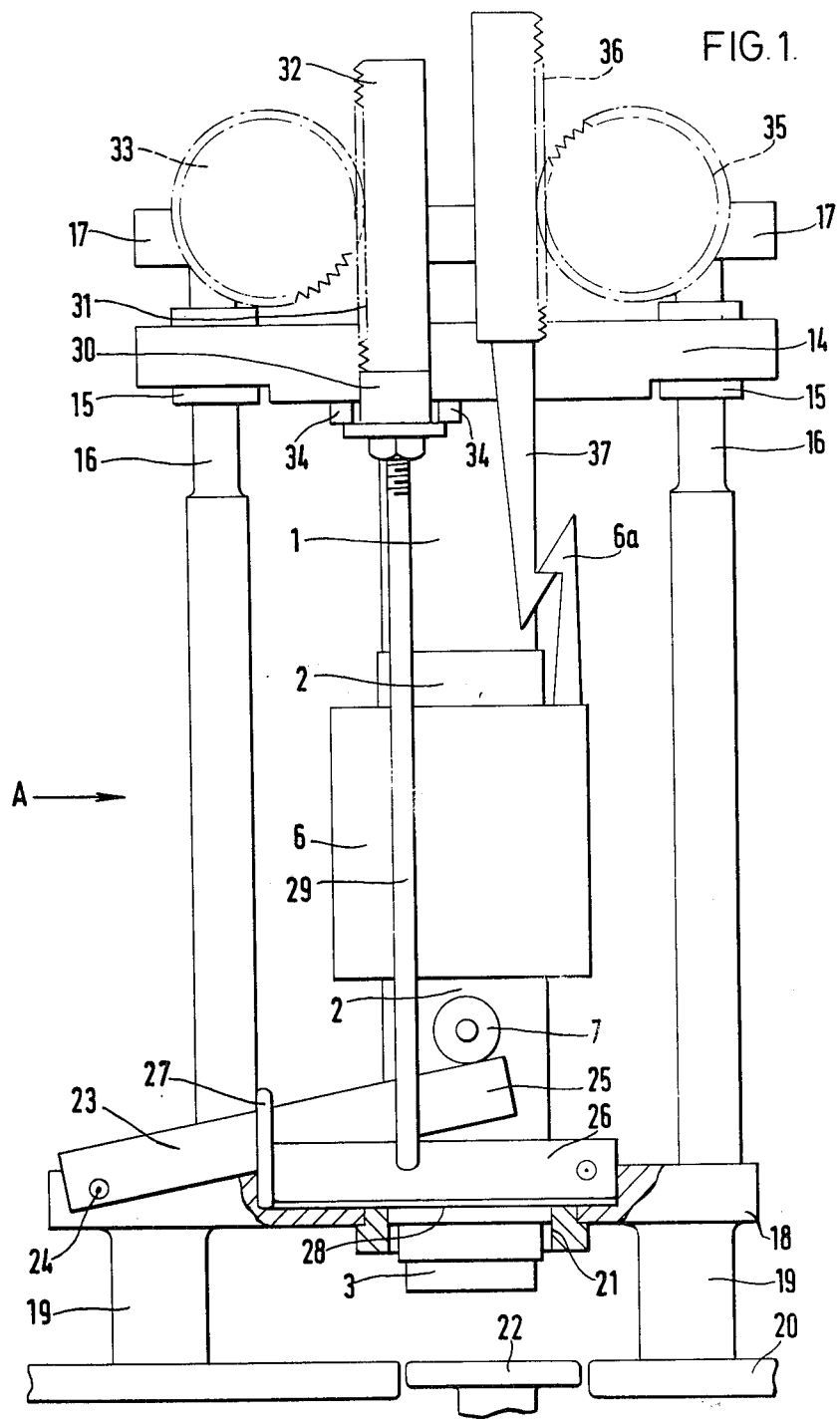
Figure 3:
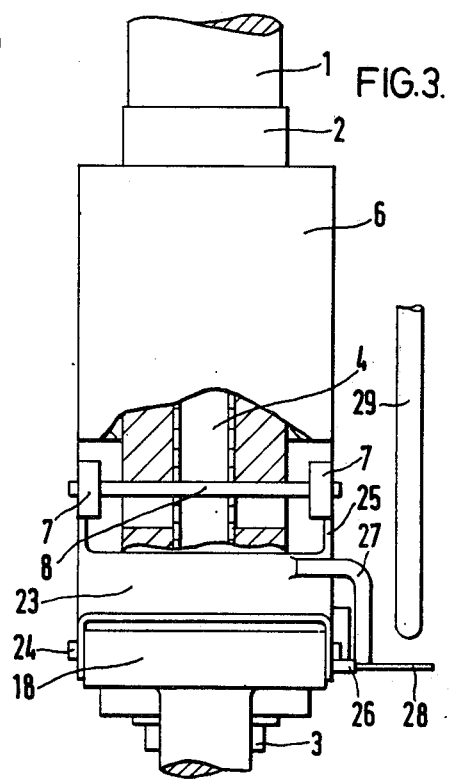
FIG. 3 is a view in the direction A of FIG. 1.

Attached to the table 18 is a mechanism whereby, except when an indentation measurement is being made, the lowest extremity of the indentor is held at least 0.1 mm above the datum surface of the foot. FIGS. 1 and 3 show the various parts of the mechanism in the positions which they occupy when both the foot 3 and the collar 6 are raised. The mechanism comprises a flanged plate 23 pivoted at 24 to the edge of table 18 and such that the flanges extend an arms 25 on each side of the housing 2 and engage with the undersides of the rollers 7. The plate spring is loaded for rotation about the pivot 24 in an anticlockwise direction (as seen in FIG. 1), thus holding the shaft 8 against the top of the slot in the housing and the ball 5 of the indentor above the datum surface of the foot. The mechanism also includes a flanged strip 26 pivoted at one end to the edge of table 18 and having at its other end a hook 27 which engages with the upper surface of the plate 23. The strip 26 presents a flange 28 for cooperation with the lower end of a vertically displaceable rod 29.

At its upper end, the rod 29 is screwed into a flanged cylindrical piece 30 which in turn is fixed to the lower end of a rack 31 vertically displaceable in a casing 32 attached to the sides of the fixed crosshead 17. The rack 31 cooperates with a pinion 33 having a spindle (not shown) suitably mounted on the crosshead 17 and driven by an electric motor (not shown). Attached to the underside of the moveable crosshead 14 is a forked bracket 34, the separation of the forks being such that they are restable (as shown in FIG. 1) on the flange of the piece 30, but also such that they are free of the sides of the main body of the piece 30.

A pinion 35 driven by an electric motor (not shown) cooperates with a second rack 36 having, depending from its lower end, a hooked arm 37, the hook of which is engageable with the hook 6a.

The operation of the apparatus is as follows: compressed gas is supplied to the manifolds 9 via connectors 10, and, with the crosshead 14 and the collar 6 in their respective upper positions, a sample 38 is placed on the turntable 22. Actuation of the appropriate drive motor rotates pinion 33 in a clockwise direction (as seen in FIG. 1), thus causing rack 31, the crosshead 14 and the housing (1 and 2) to descend. As the housing descends, the plunger 4 is carried with it by virtue of the abutment of the shaft 8 against the top of the slot in the housing. The plate 23 is simultaneously depressed but the hook 27 remains in engagement with its upper surface, the strip 26 being freely pivotable.

The descent of the housing and crosshead 14 continues until the datum surface of the foot 3 comes to rest against the sample. Thereafter the rack 31 continues to descend so that the flange of the piece 30 disengages from the forked bracket 34, and the lower end of the rod 29 contacts the flange 28. Continued action of the rod 29 on the flange 28 causes rotation of the strip 26 in an anticlockwise direction and rotation of the plate 23 in a clockwise direction, thus sequentially lowering the indentor into contact with the sample surface and disengaging the arms 25 from the rollers 7. A limit switch (not shown) operates to stop the descent of the rack and rod 29 almost immediately following such disengagement. At this time, the plunger 4 is supported only laterally against a gas cushion so that the force on the sample (the contact force) is the weight of the indentor.

According to British Standard 903: Part A 26:1969, the contact force is maintained for 5 seconds, (i.e. the first determined period of time is 5 seconds). At the end of this period, transducer output is sampled to obtain a measure of the indentation. The indenting force increment is then applied to the indentor by lowering the second rack 36 so that the collar 6 descends and comes to rest on the rollers 7. A limit switch (not shown) operates to stop the descent of the rack 36 shortly after uncoupling of the hook on the arm 37 from the hook 6a. For a test carried out in accordance with the aforesaid standard, the second determined period of time, i.e. the time during which the weight of the collar is carried on the rollers, is 30 seconds. At the end of this period, the transducer output is again sampled. Thereafter the collar 6, and the crosshead 14 and the housing are raised to their upper positions by their respective rack and pinion drives, and the turntable 22 is rotated through approximately 60°. The foot and the indentor are then lowered into contact with the newly presented portion of sample surface, and the sequence is repeated. The sequence is repeated at a third portion of the sample surface and the sample is then removed from the turntable.

In an automatic apparatus, control and presentation of results can be provided by an electronic module providing the functions of sequencing of the mechanical handling and measuring apparatus, including triggering of the analogue to digital convertors, and of controlling the operation of a printer driver assembly which computes the median of the three or more measurements carried out on the sample and prints the results on printer paper.

The sequencing unit includes a sequencing counter driven by a one second period oscillator, and which at the appropriate times acuates relays to operate the rack and pinion drives, actuates the turntable rotation mechanism, commands measurement of the indentation at the end of the first determined time period, and commands measurement of the indentation at the end of the second determined time period. In apparatus designed to carry out measurements on several samples stored in a cassette, the functions of the sequencing unit can be extended to actuation of mechanisms by means of which the samples are taken one at a time from the cassette and transferred to the turntable, removed from the turntable, and optionally returned to the cassette.

Figure 4:
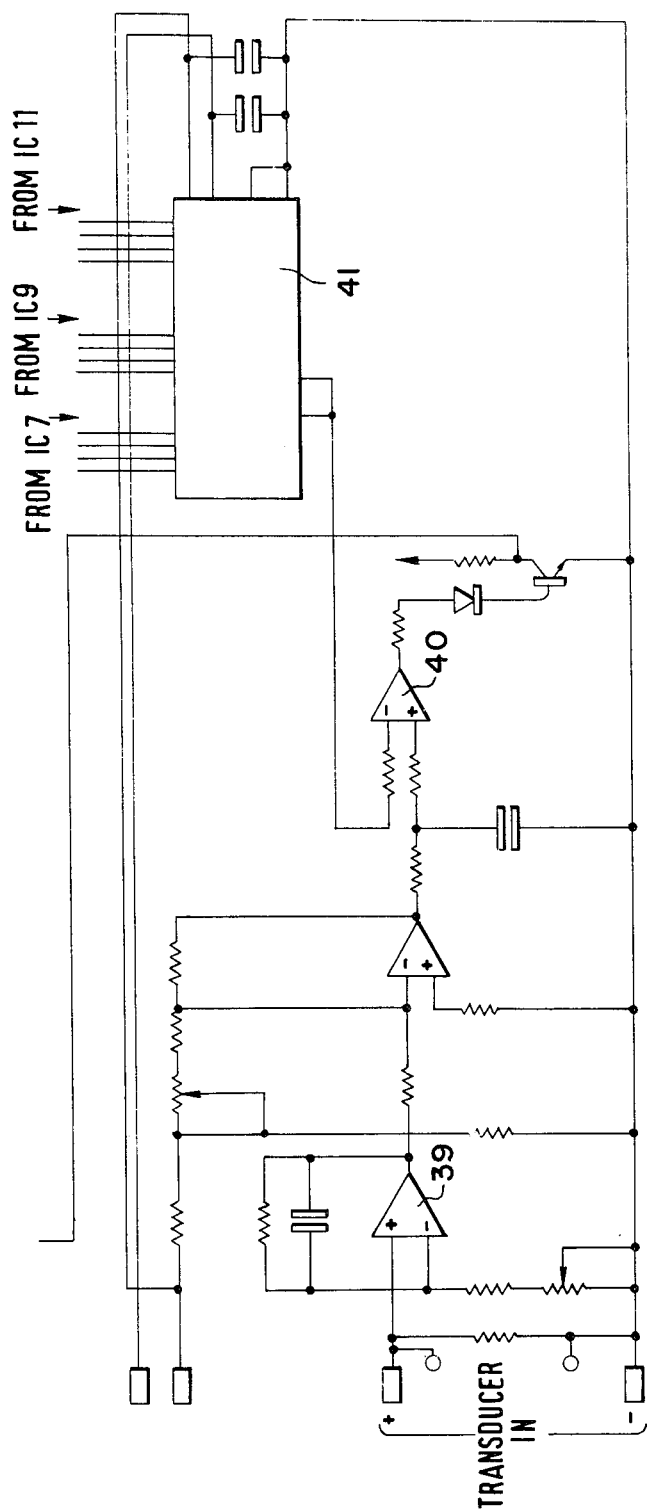
FIG. 4 is a diagram of part of the circuit used to convert the electrical output signal from the transducer to International Rubber Hardness Degrees.
Figure 5:
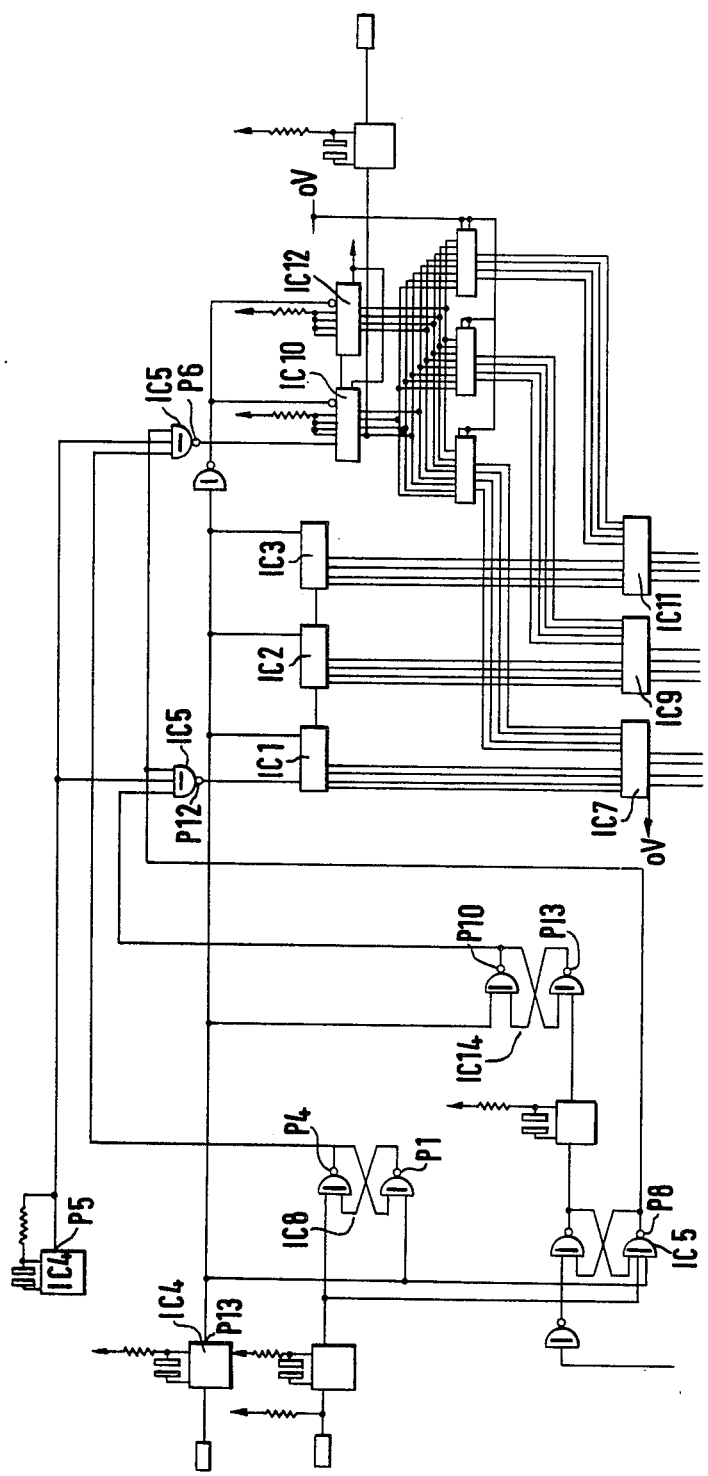
FIG. 5 is a diagram of another part of the said circuit.

The purpose of the circuitry (the convertor) shown in FIGS. 4 and 5 is to convert the difference between the indentation by a preload and the indentation by a main load into an equivalent hardness number in IRHD according to the standard relationship.

The convertor combines, in effect two analogue to digital convertors whose outputs are added together until a digital number is obtained which, when converted to the analogue form, compares exactly with the input from a transducer. One of the convertors has, instead of the conventional counter, a counter which performs the function of addressing a digital 256 word, 12 bit read-only store. The store is programmed such that the relationship between input address and output binary number has the required non-linear fuction. Indentation values for hardness (IRHD) in ½ degree intervals are stored in successive locations of the store.

The actual hardness obtained is found by dividing by two the store address obtained when a complete conversion has been made. Rounding to the nearest whole degree is achieved by regarding an odd numbered (least significant bit equal one) address as the triggering condition for the divide by two circuitry elsewhere.

Analogue signals from the displacement transducer are received at the input of amplifier 39 where they are offset, and amplified such that one micron of indentation corresponds exactly to one binary bit in the store to reduce rounding errors. The output from amplifier 39 is fed to one side of a comparator 40. The output from a 12 bit digital to analogue convertor 41 is fed to the other side of the comparator 40. The circuit includes a monostable IC 4, an address counter formed by IC 10 and IC 12 and a counter A formed by IC 1, IC 2, and IC 3, IC 4 providing a narrow pulse to reset both the address counter and counter A. The circuit is instructed to measure the preload indentation at IC 4 pin P 13, and while measuring preload indentation, the address counter is reset and counter A is incremented by enabling pulses from a clock source at IC 4 pin P 5 through IC 5 pin P 12 to counter A clock input. IC 5 pin P 12 is inhibited when balance is obtained until the next measurement of preload indentation. The output of counter A is added to the store output by IC 7, IC 9 and IC 11 and then converted to analogue form in convertor 41.

Application of the main load unbalances the comparator, and with the digital equivalent of the preload indentation held as described above, the address counter is clocked by a similar process until a new balance for main load indentation is obtained. Control of the enabling inputs to IC 5 pin P 12 and IC 5 pin P 6 is made by the bistables formed by IC 8 (outputs on pins P 4 and P 1), IC 14 (outputs on pins P 10 and P 13), IC 10 pin P 4 and IC 5 pin P 8. Hardness in IRHD is found by dividing by two (using circuitry not shown) the output of the address counter.

The embodiments of the invention in which an exclusive property or privilege is claimed are defined as follows:

1. Apparatus for measuring the hardness of a sample of rubber, comprising a sample support surface, an indentor comprising a plunger terminating in a probe and having its axis perpendicular to the support surface, a housing within which the plunger is a sliding fit, means for introducing gas under pressure between the bearing surfaces of the plunger and the housing, a foot providing a datum surface that is flat and normal to the indentor axis, the foot being such as to allow free passage of the probe therethrough, means for lowering the foot into contact with a sample, means for lowering the probe into contact with the same such that the indentor is free standing on the sample and exerts on the sample a determined contact force for a first determined period of time, means applicable to the indentor to increase the weight on the sample by the indenting force increment for a second determined period of time, and means to indicate the downward movement of the indentor during the said second determined period of time; said apparatus further including a transducer which provides electrical signals indicative of the position of the indentor relative to the housing, and an electrical circuit including a linear analogue to digital convertor which obtains and stores a digital number corresponding to the position of the indentor in contact with the sample at the end of the first said period of time, and a non-linear analogue to digital convertor which includes a digital store in the form of a "table" giving the non-linear correlation defined in the Standards between indentation (converted to an analogue input signal) and International Rubber Hardness Degrees presented as a digital output.

2. Apparatus of claim 1, further characterized in that the sample support surface is supported on a turntable set eccentrically relative to the axis of the housing, and means are provided to rotate the turntable sequentially through about 60 degrees, whereby new surfaces of the sample are presented for testing.

* * * * *